United States Patent
Kim et al.

(10) Patent No.: US 8,536,358 B2
(45) Date of Patent: Sep. 17, 2013

(54) SCAFFOLD MATERIALS-TRANSITION METAL HYDRIDE COMPLEXES, INTERMEDIATES THEREFOR AND METHOD FOR PREPARING THE SAME

(75) Inventors: Jong Sik Kim, Daejeon (KR); Dong Wook Kim, Daejeon (KR); Dong Ok Kim, Seoul (KR); Gui Ryong Ahn, Daejeon (KR); Jeasung Park, Daejeon (KR); Hyo Jin Jeon, Incheon (KR); Jisoon Ihm, Seoul (KR); Moon-Hyun Cha, Seoul (KR)

(73) Assignee: Hanwha Chemical Corporation, Seoul (KR)

( * ) Notice: Subject to any disclaimer, the term of this patent is extended or adjusted under 35 U.S.C. 154(b) by 262 days.

(21) Appl. No.: 13/059,345

(22) PCT Filed: Jan. 22, 2010

(86) PCT No.: PCT/KR2010/000416
§ 371 (c)(1),
(2), (4) Date: May 9, 2011

(87) PCT Pub. No.: WO2010/085108
PCT Pub. Date: Jul. 29, 2010

(65) Prior Publication Data
US 2011/0201834 A1    Aug. 18, 2011

(30) Foreign Application Priority Data

Jan. 23, 2009  (KR) .................. 10-2009-0006205
Oct. 15, 2009  (KR) .................. 10-2009-0098159
Dec. 16, 2009  (KR) .................. 10-2009-0125357

(51) Int. Cl.
*C07F 9/00* (2006.01)
*C07F 7/00* (2006.01)
*C07F 5/00* (2006.01)

(52) U.S. Cl.
USPC ................... 556/9; 556/42; 556/51; 556/170; 556/186; 556/400; 977/742; 977/847

(58) Field of Classification Search
USPC ......... 556/42, 51, 170, 186, 400, 9; 977/742, 977/847
See application file for complete search history.

(56) References Cited

U.S. PATENT DOCUMENTS 3,285,898 A * 11/1966 MacKenzie et al. ............ 526/96
6,821,783 B1   11/2004 Comely et al.
2007/0032629 A1  2/2007 Banet et al.

FOREIGN PATENT DOCUMENTS

KR    1020080024975 A    3/2008
KR    1020080024976 A    3/2008

(Continued)

OTHER PUBLICATIONS

Vidal et al., Science, vol. 276, pp. 99-102 (1997).*
(Continued)

*Primary Examiner* — Porfirio Nazario Gonzalez
(74) *Attorney, Agent, or Firm* — The Webb Law Firm

(57) ABSTRACT

The present invention relates to substances which can be applied to the technical fields of gas storages, polymerization catalysts and optical isomers, their intermediates, and processes for preparing the same, which is characterized in that 1) possible disintegration of structure of the scaffold material (SM) is impeded, and 2) they are prepared by a simple manufacturing system as compared to the substances conventionally suggested in the application field. Specifically, it relates to scaffold material-transition metal hydride complexes comprised of scaffold material (SM) and transition metal hydride ($M^1H_{(n-1)}$) which is chemically bonded to the functional groups formed on the scaffold material, SM-transition metal halide complex and SM-transition metal ligand complex as the precursors, and a process for preparing the same. The SM-transition metal hydride complex according to the present invention is a substance for hydrogen storage which adsorbs hydrogen via Kubas adsorption. The complex according to the invention can store high capacity of hydrogen with safety and reversibility, while disintegration of its structure does not occur even with repeated adsorption-desorption of hydrogen.

20 Claims, 3 Drawing Sheets

(56) References Cited

FOREIGN PATENT DOCUMENTS

| | | |
|---|---|---|
| KR | 1020090095245 A | 9/2009 |
| KR | 1020100019653 A | 2/2010 |
| WO | 03046019 A1 | 6/2003 |
| WO | 2008032985 A1 | 3/2008 |

OTHER PUBLICATIONS

Brunel et al., Coordination Chemistry Reviews, vol. 178-180, pp. 1085-1108 (1998).*

* cited by examiner

SCAFFOLD MATERIALS-TRANSITION METAL HYDRIDE COMPLEXES, INTERMEDIATES THEREFOR AND METHOD FOR PREPARING THE SAME

TECHNICAL FIELD

The present invention relates to substances which can be applied to the technical fields of gas storages, polymerization catalysts and optical isomers, their intermediates, and processes for preparing the same. Specifically, the invention provides scaffold material-transition metal hydride complexes comprised of scaffold material (SM) and transition metal hydride ($M^1H_{(n-1)}$) which is chemically bonded to the functional groups formed on the scaffold material, SM-transition metal halide complex and SM-transition metal ligand complex as the precursors, and a process for preparing the same.

As a representative application, the material according to the invention can be employed as a substance which can adsorb hydrogen molecule via Kubas adsorption. The substance can be used as hydrogen storage medium for operating medium to small sized fuel cells since 1) possible disintegration of structure of the scaffold material (SM) is impeded, and 2) adsorption/desorption of hydrogen can be carried out under relatively mild condition (for example, adsorption at 25° C., 30 atm, desorption at 100° C., 2 atm) as compared to various hydrogen storage materials which have been conventionally known.

BACKGROUND ART

Recently, importance of green energy has come up as a solution to overcome exhaustion of fossil fuel and problem of global warming, and studies regarding thereto have been actively processed. Specifically, studies on green energy are progressed in two discriminate fields: the one is energy development due to natural phenomenon such as solar energy, wind power and tidal power; and the other is development of novel recycled energy such as bio-energy and hydrogen.

The most significant requisites for energy nowadays include 1) environmental friendliness, 2) reversible conversion and recycling, 3) applicability to motor vehicles such as automobiles and aircraft, and generating facilities in a large scale, and 4) availability to any place any time.

Hydrogen energy, that meets best the four requisites among green energies, is investigated in three fields: production, storage and application of hydrogen. In the field of hydrogen storage, it is focused to develop media that 1) satisfies 6 wt % of capacity suggested by DOE of United States as guideline in 2010; and 2) safely and reversibly stores a large volume of hydrogen.

Though hydrogen storage media suggested by a plurality of investigation groups are very diverse and complicated, they can be classified, depending upon the adsorption mechanism of hydrogen on the hydrogen storage media and the relevant adsorption energy range, into three: physisorption, Kubas adsorption and chemisorption.

The hydrogen storage materials by physisorption include porous substances having micro/medium pore, such as microporous (2 nm or less) and mesoporous (2~50 nm) substances, which are further classified into carbon substances, inorganic oxides and metal-organic frameworks (MOF). The metal-organic framework essentially comprises metal salt and organic linker as the backbone. The coordinate structure formed by metal ion and organic linker may be a simple molecule formed by self-assembly, or in various forms such as one-dimensional (linear), two-dimensional (planar) and complicated three-dimensional structures. Since the porous materials store hydrogen in the pores of the material, they adsorb hydrogen in a proportional relevancy to the surface area (adsorption type I), having weak adsorption energy of not more than about 10 KJ/mol. In order to increase such weak adsorption energy (10 KJ/mol) to enable adsorption of a significant amount of hydrogen even at extremely low temperature or higher, doping with various precious metal (Pt, Pd, Ru, Rh) or transition metal (Co, Ni, Ti) has been investigated. However, the processes of physisorption involve difficulties to be commercially used due to 1) hydrogen storage that cannot achieve the standard (6 wt %) of minimum hydrogen storage suggested by Department of Energy (DOE) in the United States for practical use of hydrogen storage material, 2) low reproducibility of hydrogen storage, 3) harsh conditions required for hydrogen adsorption (extremely low temperature, for example, 100K or lower), and/or 4) relatively harsh conditions for hydrogen adsorption/desorption, and disintegration of materials being occurred during the course of adsorption/desorption of hydrogen.

Substances for hydrogen storage by chemisorptions may be classified into 1) alanate, LaNi type metal hydrides (50-100 KJ/mol), and 2) chemical hydrides (100 KJ/mol or more) such as $NaBH_4$ and $Ca(BH_4)_2$. They store hydrogen by themselves in the internal structure of the materials, having strong adsorption energy of about 50 KJ/mol or more. However, they also involve difficulties to be commercially used due to 1) hydrogen storage that cannot achieve the standard (6 wt %) of minimum hydrogen storage suggested by Department of Energy (DOE) in the United States for practical use of hydrogen storage material, 2) low reproducibility after repeated adsorption/desorption of hydrogen and viability of disintegration of the structure, 3) difficulties in reversible reproduction, and/or 4) harsh conditions required for hydrogen adsorption/desorption (high temperature and/or high pressure).

In the technical field of hydrogen storage materials, those adsorbing hydrogen molecules by Kubas adsorption mechanism are considered as excellent storage media since they can adsorb hydrogen molecules at the temperature and pressure range close to ambient temperature and pressure, differently from conventionally reported materials adsorbing hydrogen on the basis of physisorption or chemisorption.

The monomeric or polymeric organometallic or coordination compounds and organic-transition metal hydride complexes, suggested by Hanwha Chemical R&D Center in Korean Patent Applications are suitable for commercial use because 1) they can store hydrogen with high capacity and high efficiency, 2) they can enable hydrogen adsorption/desorption under milder condition (for example, adsorption at 25° C., 30 atm and desorption at 100° C., 2 atm), and 3) there is no significant disintegration of the structure after repeated adsorption/desorption of hydrogen, as compared to hydrogen storage material conventionally suggested by means of Kubas binding. [See Korean Patent Application Nos. 10-2007-0090753, 10-2007-0090755, 10-2008-0020467, 10-2008-0078334.]

In case of said organic-transition metal hydride complexe, however, spontaneous aggregation of a part of the complex may occur owing to insufficient chemical stability, to be converted into a multimeric organic-transition metal complex having the molecular weight of an oligomer or more.

DISCLOSURE OF INVENTION

Technical Problem

The object of the present invention is to provide scaffold material-transition metal hydride complexes being applicable to the technical fields of gas storage, polymerization catalysts and optical isomers.

Another object of the invention is to provide a process for preparing scaffold material-transition metal hydride complexes by establishing a simpler system for preparing the complexes with impeding possible disintegration of the structure of the scaffold material.

Still another object of the invention is to provide certain novel intermediates for preparing the materials applicable to the above-mentioned technical fields.

Still another object of the invention is to provide novel hydrogen storage material, which can retain hydrogen storage capability after repeated hydrogen adsorption/desorption with prominently enhanced chemical stability, by overcoming the problems of conventional organic transition metal hydride complexes (that is, aggregation of metals themselves may occur during repeated hydrogen adsorption/desorption, or polymerization of the complexes may occur owing to such aggregation, thereby possibly resulting in decrease of hydrogen storage capability), and a process for preparing the same.

Solution to Problem

The present invention relates to substances which can be applied to the technical field of gas storages, polymerization catalysts and optical isomers, their intermediates, and processes for preparing the same. Specifically, the invention provides scaffold material-transition metal hydride complexes comprised of scaffold material (SM) and transition metal hydride ($M^1H_{(n-1)}$) which is chemically bonded to functional groups formed on the scaffold material, SM-transition metal halide complex and SM-transition metal ligand complex as the precursors, and a process for preparing the same.

Further, according to the present invention, excellent chemical stability as hydrogen-storage material could be ensured by using scaffold material (SM) with excellent chemical stability, instead of alkyl group or aryl group bonded to transition metal in conventional organic-transition metal hydride complexes. Specifically, complexes having the structure, in which transition metal hydride is chemically bonded to functional groups formed on the surface of the scaffold material such as inorganic oxide, carbon substance or metal organic framework (MOFs), are used as hydrogen-storage material, to avoid the problem of reduced hydrogen adsorption owing to aggregation or deterioration of transition metal. In addition, the complexes according to the invention are chemically stable due to strong bonding strength between the scaffold material and transition metal, with high capability of adsorbing hydrogen even at room temperature, and the structure can be stably retained without deformation under repeated adsorption and desorption of hydrogen.

When porous material is used for such scaffold material, expected can be physical adsorption of additional hydrogen due to large surface area, with an advantage of robust structure with high stability under relatively severe condition of oxidative or reductive reaction.

Now, the present invention is described in more detail.

The technical and scientific terms used herein, if not stated otherwise, are understood to have common meaning acknowledged by a person having ordinary skill in the technical field to which the present invention belongs. Repeated descriptions regarding technical constitution and effect being identical to those of conventional technique are omitted.

One aspect of the present invention relates to a scaffold material-transition metal hydride complex represented by Chemical Formula (1), which is comprised of scaffold material (SM), and transition metal hydride ($M^1H_{(n-1)}$) which is chemically bonded to functional groups formed on the surface of the scaffold material:

$$[SM]\text{-}M^1H_{(n-1)} \qquad \text{[Chemical Formula 1]}$$

wherein [SM] represents scaffold material containing functional groups on the surface, $M^1$ represents transition metal having the valency of at least 2, and n represents the valency of $M^1$.

The complexes according to the present invention have the structure in which transition metal hydride is bonded to a scaffold material. Transition metal hydride may be bonded to all or part(s) of the functional groups depending upon the type of SM, type of functional groups to be dehydrogenated, reaction condition and amount of the reactants.

The functional groups formed on the surface of SM in the present invention can be ordinarily formed during the preparation of SM, or formed via additional modification. Specific examples of one or more functional groups include —OH, —SH, —COOR$^{21}$, —NH$_2$, —HNR$^{22}$, —NR$^{23}$R$^{24}$, —PH$_2$, —PHR$^{25}$, —PR$^{26}$R$^{27}$, —SO$_3$R$^{28}$, —PO$_3$HR$^{29}$ and —PO$_3$R$^{30}$, wherein R$^{21}$, R$^{28}$ and R$^{29}$ independently represent hydrogen or alkali metal, R$^{22}$ through R$^{27}$ are independently selected from (C1-C20)alkyl, (C3-C8)cycloalkyl, (C6-C20)aryl, (C6-C20)ar(C1-C20)alkyl and (C1-C20)alkyl(C6-C20)aryl group, and R$^{30}$ preferably represents alkaline earth metal. More specifically, the functional groups may be one or more group(s) selected from —OH, —SH, —COOH and —NH$_2$, which can easily react with transition metal compound in dehydrogenation.

In Chemical Formula (1), $M^1$ represents transition metal having the valency of at least 2, and $M^1$ may comprise single type of metal element or different kinds of metal elements. Preferably, $M^1$ is one or more metal selected from titanium (Ti), vanadium (V) and scandium (Sc), which can make Kubas binding; n is an integer from 2 to 6, and (n−1) specifically is an integer from 1 to 5, more specifically an integer from 2 to 4, most specifically 3.

The scaffold material of the present invention can be selected from inorganic oxides, carbon substances and metal organic frameworks (MOFs). The inorganic oxide or carbon substance may have the pore size in order to avoid aggregation of transition metal halide or transition metal hydride. The pore size may be micropore (2 nm or less), mesopore (2~50 nm) or macropore (50 nm or more), not being strictly restricted. It is preferable to use scaffold material which is stable so that the structure would not be disintegrated under relatively harsh condition of oxidative or reductive reaction, having very low solubility in polar and nonpolar solvent to facilitate separation and purification.

The inorganic oxide may be selected from one or more metal oxide(s) selected from a group consisting of Ti, Al, Si, V, Zr, Nb, Hf and Ta, and mixtures thereof. Specifically, it may be silica, titania, zirconia or zeolite, preferably mesoporous silica.

The carbon substance may be selected from carbon nanotubes, graphite, carbon nanofiber, carbon nanohorn, fullerence and mixtures thereof. Multi-wall carbon nanotube may be preferably used.

The SM selected from inorganic oxides and carbon substances may be those having been doped or incorporated by one or more substance(s) selected from B, P, Li, Na, K, Rb, Cs, Fr, Be, Mg, Ca, Sr, Ba, Ra, F, Cl, Br, I and transition metals. For such doping or incorporation, type of substance is determined in order to meet the use without altering physical properties of the inorganic oxide or carbon substance, and the amount of doping or incorporation may be controlled within the range not to deteriorate physical stability, and conventional method for doping or incorporation can be adopted. According to the invention, the performances in the applicable fields can be enhanced by such doping or incorporation.

Metal organic framework, being a nanoporous substance, has very well-defined pores, as well as very large surface area and pore volume with solid structure. The pore size and chemical environment inside the pore can be easily controlled by selecting suitable linker, that is, bidentate compound, tridentate compound or polydentate compound (with more linkage). Metal organic frameworks have excellent heat resistance and chemical resistance.

The metal organic frameworks (MOFs) are characterized by comprising metal ($M^2$) and organic linker ($L^1$) as the framework substance. Oxygen atom may or may not be contained depending on the structure and composition. MOFs are specifically represented by Chemical Formula (6):

$$M^2_p O_q L^1_r \qquad \text{[Chemical Formula 6]}$$

wherein, $M^2$ represents a metal ion, O represents oxygen atom, and $L^1$ represents an organic linker (linker, $L^1$) having a functional group being capable of dehydrogenation. Number q is determined depending upon the structure of the MOF, being an integer from 0 to 10. It is 1 in case of a normal cubic structure. Numbers p and r represent an integer from 1 to 10, respectively, determined by the valency of $M^2$ and number of dents of $L^1$. For example, the metal organic framework prepared by using bivalent zinc ion ($Zn^{2+}$) as metal ion and a bidentate linker can be represented by molecular formula of $Zn_4OL^1_3$. However, any metal organic framework material containing organic linker ($L^1$) having additional functional group being capable of chemical bonding with transition metal is usable, since the metal organic framework material used according to the present invention is purposed to provide structural scaffold material for transition metal hydride complex. The organic linker ($L^1$), serving as a crosslink between metals ($M^2$) in MOF, comprises at least bidentate functional group (which is linkable to metal ion ($M^2$)) such as dicarboxylate, as well as one or more additional reactive site(s) which can react with the transition metal ($M^1$) compound after forming the metal-organic framework.

Specifically, organic linker ($L^1$) may be selected from compounds represented by Chemical Formula (7), containing functional group in the framework ($G^1$) which is linkable to metal ($M^2$) ion, as well as framework surface functional group ($G^2$), which would link to transition metal ($M^1$) of the transition metal hydride ($M^1H_{(n-1)}$) during the subsequent stage.

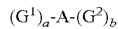

$$(G^1)_a\text{-}A\text{-}(G^2)_b \qquad \text{[Chemical Formula 7]}$$

wherein, A is selected from (C1-C20)alkylene, (C3-C8) cycloalkylene, (C6-C20)arylene, (C6-C20)ar(C1-C20)alkylene, (C1-C20)alkyl(C6-C20)arylene and (C8-C20) fused ring, the (C2-C20)alkylene may comprise unsaturated bonds, the carbon atom of arylene or alkylene may be replaced by an heteroatom selected from N, O, S and Si, and the arylene or alkylene may be further substituted by a substituent selected from —(CO)$R^{31}$, —(SO$_2$)$R^{32}$, —(CO$_2$)$R^{33}$, —S$R^{34}$, —NO$_2$, —Si($R^{35}$)($R^{36}$)($R^{37}$) and —B$R^{38}$;

$G^1$ represents carboxylate (—COO—), a is an integer from 2 to 4;

$G^2$ is selected from a group consisting of —OH, —SH, —COO$R^{41}$, —NH$_2$, —HN$R^{42}$, —N$R^{43}R^{44}$, —PH$_2$, —PH$R^{45}$, —P$R^{46}R^{47}$, —SO$_3R^{48}$, —PO$_3$H$R^{49}$ and —PO$_3R^{50}$, b is an integer from 1 to 15;

$R^{31}$ through $R^{38}$ and $R^{42}$ through $R^{47}$ are independently selected from (C1-C20)alkyl, (C3-C8)cycloalkyl, (C6-C20) aryl, (C6-C20)ar(C1-C20)alkyl and (C1-C20)alkyl(C6-C20) aryl, $R^{41}$, $R^{48}$ and $R^{49}$ independently represent hydrogen or alkali metal, and $R^{50}$ represents alkaline earth metal.

In Chemical Formula (7), A is selected from phenylene, naphthylene, biphenylene, terphenylene, anthrylene, pyrenylene and perylenylene, which may be further substituted by a substituent selected from —(CO)$R^{31}$, —(SO$_2$)$R^{32}$, —(CO$_2$)$R^{33}$, —S$R^{34}$, —NO$_2$, —Si($R^{35}$)($R^{36}$)($R^{37}$) and —B$R^{38}$; $R^{31}$ through $R^{38}$ are independently selected from (C1-C20)alkyl, (C3-C8)cycloalkyl, (C6-C20)aryl, (C6-C20) ar(C1-C20)alkyl and (C1-C20)alkyl(C6-C20)aryl; a is in integer of 2 or 3, and b is an integer from 1 to 10.

Structural formulas of organic compounds which are preferably used as organic linker ($L^1$) in the metal organic framework are shown below, but the exemplary compounds do not limit the content or scope of the present specification.

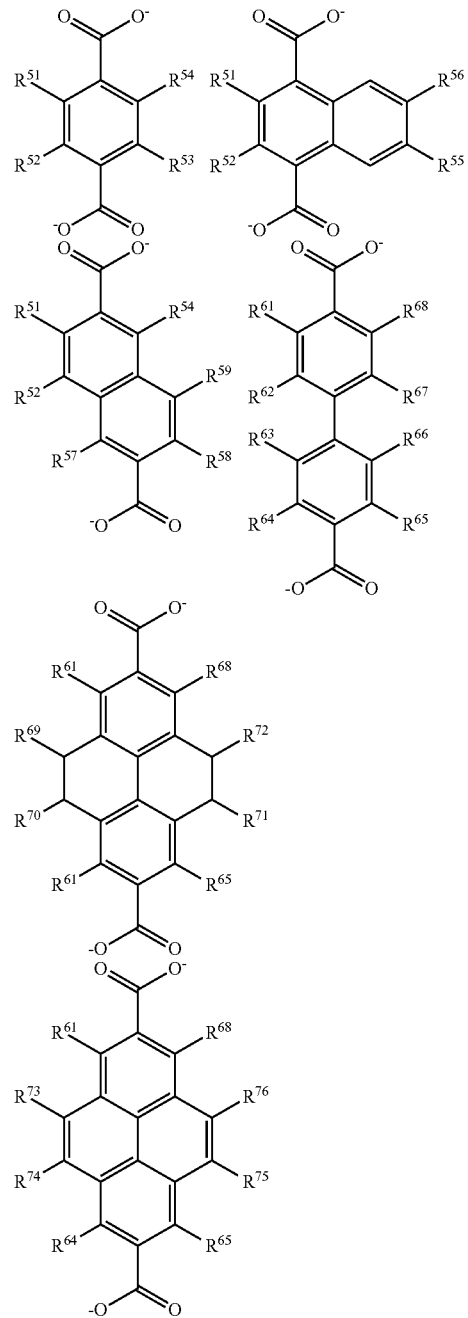

-continued

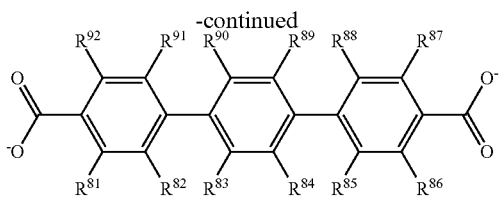

Any one or more substituent(s), $R^{51}$ through $R^{59}$, $R^{61}$ through $R^{76}$ and $R^{81}$ through $R^{92}$ in each structural formula as the framework surface functional group ($G^2$) may be selected from —OH, —SH, —COOR$^{41}$, —NH$_2$, —NHR$^{42}$, —NR$^{43}$R$^{44}$, —PH$_2$, —PHR$^{45}$, —PR$^{46}$R$^{47}$, —SO$_3$R$^{48}$, —PO$_3$HR$^{49}$ and —PO$_3$R$^{50}$, $R^{42}$ through $R^{47}$ are independently selected from (C1-C20)alkyl, (C3-C8)cycloalkyl, (C6-C20)aryl, (C6-C20)ar(C1-C20)alkyl and (C1-C20)alkyl (C6-C20)aryl, $R^{41}$, $R^{48}$ and $R^{49}$ independently represent hydrogen or alkali metal, and $R^{50}$ represents alkaline earth metal.

The metal organic framework may be prepared according to conventional method, that is, reaction of metal ion compound with organic linker in the presence of solvent. Metal ion ($M^2$) of the metal ion compound includes those belonging to Group 1 to Group 16 of the Periodic Table of Elements. On or more metal ion(s) selected from Li$^+$, Na$^+$, K$^+$, Rb$^+$, Be$^{2+}$, Mg$^{2+}$, Ca$^{2+}$, Sr$^{2+}$, Ba$^{2+}$, Sc$^{3+}$, Y$^{3+}$, Ti$^{4+}$, Zr$^{4+}$, Hf$^{4+}$, V$^{4+}$, V$^{3+}$, V$^{2+}$, Nb$^{3+}$, Ta$^{3+}$, Cr$^{3+}$, Mo$^{3+}$, W$^{3+}$, Mn$^{3+}$, Mn$^{2+}$, Re$^{3+}$, Re$^{2+}$, Fe$^{3+}$, Fe$^{2+}$, Ru$^{3+}$, Ru$^{2+}$, Os$^{3+}$, Os$^{2+}$, Co$^{3+}$, Co$^{2+}$, Rh$^{2+}$, Rh$^+$, Ir$^{2+}$, IR$^+$, Ni$^{2+}$, Ni$^+$, Pd$^{2+}$, Pd$^+$, Pt$^{2+}$, Pt$^+$, Cu$^{2+}$, Cu$^+$, Ag$^+$, Au$^+$, Zn$^{2+}$, Cd$^{2+}$, Hg$^{2+}$, Al$^{3+}$, Ga$^{3+}$, In$^{3+}$, Tl$^{3+}$, Si$^{4+}$, Si$^{2+}$, Ge$^{4+}$, Ge$^{2+}$, Sn$^{4+}$, Sn$^{2+}$, Pb$^{4+}$, Pb$^{2+}$, As$^{5+}$, As$^{3+}$, As$^+$, Sb$^{5+}$, Sb$^{3+}$, Sb$^+$, Bi$^{5+}$, Bi$^{3+}$ and Bi$^+$ should be involved in the reaction.

The metal ion compound may be in the form of metal salt, and the anion which links to the metal ion in the metal salt may be conventional anion selected from those belonging to Group 14 to Group 17 of the Periodic Table of Elements. As the metal salts, mentioned may be, without restriction, metal inorganic acid salt such as metal nitrate, metal sulfate, metal phosphate and metal hydrochloride.

The second aspect of the present invention relates to a process for preparing a scaffold material-transition metal hydride complex represented by Chemical Formula (1) via hydrogenation-dehalogenation from a scaffold material-transition metal halide complex represented by Chemical Formula (2) comprised of scaffold material (SM) containing functional groups on the surface and transition metal halide ($M^1H_{(n-1)}$) which is chemically bonded to functional groups formed on the surface of the scaffold material.

[SM]-$M^1H_{(n-1)}$       [Chemical Formula 1]

[SM]-$M^1X_{(n-1)}$       [Chemical Formula 2]

wherein, [SM] represents scaffold material containing functional groups on the surface, $M^1$ represents transition metal having the valency of at least 2, X is selected from halogen elements, and n represents the valency of $M^1$.

The hydrogenation-dehalogenation can be carried out according to the preparation process described by the inventors Korean Patent Application Nos. 2007-0090753, 2007-0090755, 2008-0020467 or 2008-0078334. Otherwise, it can be achieved by hydrolysis, thermolysis, photolysis, or the like. More specifically, the process may be any of traditional synthetic processes applying various hydrogen sources such as 2-propanol, NaBH$_4$ and hydrogen (H$_2$) gas in the presence of precious metal catalyst, synthetic processes employing radical initiator and radical reductant at the same time, synthetic processes applying aluminum hydride (MAH) compound as a strong reductant and Lewis base (LB) as week base, respectively. As more preferable preparation process, mentioned may be a synthetic process wherein alkali metal, alkaline earth metal or their mixture is reacted with (C10-C20) aromatic cyclic compound in the presence of aprotic polar solvent to obtain complex reductant composition, which is then applied to the synthesis.

As a more preferable example, a process for preparing scaffold material-transition metal hydride complex to which complex reductant composition is applied is described in more detail hereinbelow.

The process for preparing scaffold material-transition metal hydride complex to which complex reductant composition is applied comprises following stages, which is carried out under argon or inert gas atmosphere:

a) reacting alkali metal, alkaline earth metal or their mixture with (C10-C20)aromatic cyclic compound in the presence of aprotic polar solvent to obtain complex reductant composition; and b) reacting the complex reductant composition with the scaffold material-transition metal halide complex to obtain scaffold material-transition metal hydride complex.

The alkali metal or alkaline earth metal has excellent reductivity. Metals selected from Li, Na, K, Rb, Cs, Fr, Mg, Ca, Sr, Ba and Ra may be used alone or as a mixture. Preferably used is alkali metal, more preferably Li.

The aromatic cyclic compound according to the present invention is one or more compound(s) selected from naphthalene, biphenyl, phenanthrene, anthracene, trans-stilbene and derivatives thereof.

More specifically, naphthalene or naphthalene derivatives may be used due to easy handling and excellent sublimation property, and easy removal after hydrogenation-dehalogenation.

The aprotic polar solvent may be one or more solvent(s) selected from tetrahydrofuran (THF), 1,2-dimethoxyethane (DME), dioxane (DXN), diethyleneglycoldimethylether (diglyme), dimethylformamide (DMF), dimethylsulfoxide (DMSO), dimethylacetamide (DMA), hexamethylphosphoramide (HMPA) and derivatives thereof. They can be used as reaction solvent and hydrogen source as well. Specifically, the aprotic polar solvent is preferably tetrahydrofuran (THF), 1,2-dimethoxyethane (DME), or derivatives thereof, used alone or as a mixture thereof, with advantage of low boiling point and easy handling.

In the hydrogenation-dehalogenation employing said complex reductant composition, the complex reductant composition reacts with the scaffold material-transition metal halide complex in the presence of aprotic polar solvent, while the complex reductant composition dehalogenates the scaffold material-transition metal halide complex and the aprotic polar solvent provides hydrogen to form the scaffold material-transition metal hydride complex.

Reaction temperature of stage b) is from −80 to 50° C., preferably from −50 to 30° C., more preferably from −30 to 25° C. If it is lower than −80° C., hydrogenation-dehalogenation may not be completely performed. If it is higher than 50° C., the product (scaffold material-transition metal hydride complex) may be decomposed.

Reaction duration of stage b) is from 1 to 72 hours, preferably from 1 to 48 hours, more preferably from 1 to 24 hours. If it is less than 1 hour, hydrogenation-dehalogenation may not be completely performed. If it is more than 72 hours, the product (scaffold material-transition metal hydride complex) may be decomposed.

The process according to the present invention may further comprise a stage for separating and purifying the scaffold material-transition metal hydride complex by using one or more nonpolar solvent selected from pentane, toluene, benzene, ether, tetrahydrofuran (THF) and derivatives thereof, after stage b). The process for separation or purification may be Schlenk method, rotary evaporation or distillation under reduced pressure. When using alcoholic solvent with high polarity during the separation and purification, separation or purification may be troublesome owing to side reactions.

Third aspect of the present invention relates to a process for preparing a scaffold material (SM)-transition metal hydride complex which is characterized in that 1) a scaffold material (SM) containing functional groups formed on the surface is reacted with an organic-transition metal precursor of Chemical Formula (4) to obtain a SM-transition metal ligand complex having the structure of Chemical Formula (3), wherein the functional groups are linked with the transition metal ligand; and 2) the SM-transition metal ligand complex is then subjected to hydrogenation to provide a SM-transition metal hydride complex having the structure of Chemical Formula (1).

[SM]-$M^1H_{(n-1)}$     [Chemical Formula 1]

[SM]-$M^1L_{(n-1)}$     [Chemical Formula 3]

$M^1L_n$     [Chemical Formula 4]

wherein, [SM] represents scaffold material containing functional groups on the surface, $M^1$ represents transition metal having the valency of at least 2, L represents an organic ligand that may be same or different from each other, or may be linked each other to be chelated to metal as a bidentate or tridentate ligand, and n represents the valency of $M^1$.

The organic-transition metal precursor employed in stage 1) comprises transition metal ($M^1$) such as Ti, Sc and V, and one or more ligands selected from atrane-type ligand, amino-type ligand, oxy-type ligand, thio-type ligand and phosphino-type ligand.

The scaffold material-transition metal ligand complex ([SM]-$M^1L_{(n-1)}$) of which the structure is represented by Chemical Formula (3) can be prepared by incorporating the solution of organic-transition metal precursor ($M^1L_n$) of Chemical Formula (4) to a dispersion of SM containing functional groups on the surface and reacting the mixture. However it is concerned that organic-transition metal precursor ($M^1L_n$) may be deformed, due to sensitive reaction with air or moisture, into irreversible oligomers (such as tetramer, hexamer), so that all reaction and purification processes are preferably carried out under atmosphere of argon, nitrogen or helium, and organic solvent is used after purifying by appropriate method. After the reaction is completed, one or two of the processes described below is (are) applied in order to remove reaction solvent and reaction byproducts, to obtain the scaffold material-transition metal ligand complex ([SM]-$M^1L_{(n-1)}$) represented by Chemical Formula (3):

a) drying in vacuo for 24 hours, more preferably 48 hours with applying Schlenk method in order to remove residual reaction solvent and organic solvent for purification [preferable organic solvent may be employed in the purification stage(s)]

b) applying chemical extraction with supercritical $CO_2$ (Korean Patent Application No. 10-2008-0044633).

The organic ligands (L) may be same or different from each other, or may be linked each other to be chelated to metal as a bidentate or tridentate ligand. Specifically the organic ligand may be alkyl-type ligand, atrane-type ligand, amino-type ligand, oxy-type ligand, thio-type ligand or phosphino-type ligand, which is selected from Z—(W—Y)$_3^{3-}$, —NH$_2$, —NHR$^1$, —NR$^1$R$^2$, —OH, —OR$^3$, —SH, —SR$^4$, —PH$_2$, —PHR$^5$, —PR$^5$R$^6$ and —(CR$^7$R$^8$)$_y$R$^9$; Z represents B, CR$^{10}$, N or SH; R$^{10}$ represents hydrogen, (C1-C20)alkyl, (C3-C8)cycloalkyl, (C6-C20)aryl, (C6-C20)ar(C1-C20)alkyl or (C1-C20)alkyl(C6-C20)aryl; W represents (C1-C20)alkylene, (C3-C8)cycloalkylene, (C6-C20)arylene, (C6-C20)ar(C1-C20)alkylene or (C1-C20)alkyl(C6-C20)arylene; Y represents NH$_2$, O or S; R$^1$ through R$^6$ independently represent (C1-C20)alkyl, (C3-C8)cycloalkyl, (C6-C20)aryl, (C6-C20)ar(C1-C20)alkyl or (C1-C20)alkyl(C6-C20)aryl; R$^7$ through R$^9$ independently represent hydrogen, (C1-C20)alkyl, (C3-C8)cycloalkyl, (C6-C20)aryl, (C6-C20)ar(C1-C20)alkyl, (C1-C20)alkyl(C6-C20)aryl, —NH$_2$, —NHR$^a$, —NR$^a$R$^b$, —OH, —OR$^c$, —SH, —SR$^d$, —PH$_2$, —PHR$^e$ or —PR$^e$R$^f$; R$^a$ through R$^f$ independently represent (C1-C20)alkyl, (C3-C8)cycloalkyl, (C6-C20)aryl, (C6-C20)ar(C1-C20)alkyl or (C1-C20)alkyl(C6-C20)aryl; y is an integer from 1 to 30; the alkylene, cycloalkylene, arylene, aralkylene or alkylarylene of W, and the alkyl, cycloalkyl, aryl, aralkyl or alkylaryl of R$^1$ through R$^9$ may be further substituted by one or more substituent(s) selected from a group consisting of —NR$^{11}$R$^{12}$, —OR$^{13}$, —CR$^{14}$R$^{15}$R$^{16}$, —SR$^{17}$ and —PR$^{18}$R$^{19}$; R$^{11}$ through R$^{19}$ independently represent hydrogen, (C1-C20)alkyl, (C3-C8)cycloalkyl, (C6-C20)aryl, (C6-C20)ar(C1-C20)alkyl or (C1-C20)alkyl(C6-C20)aryl.

The organic ligand (L) is selected from those represented by one of the following structural formulas, but it is not restricted thereto.

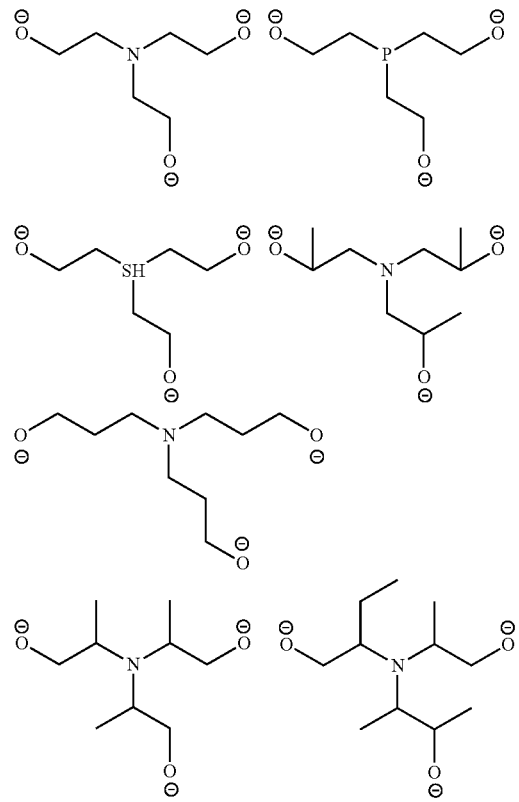

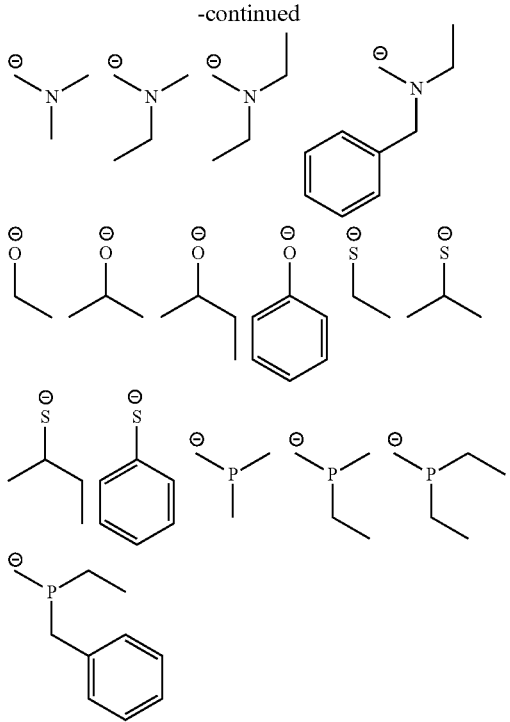

Reaction temperature of the first stage is preferably from −80 to 100° C., more preferably from −20 to 30° C. If it is lower than −80° C., decoration of the organic-transition metal precursor ($M^1L_n$) may not undergo easily. If it is higher than 100° C., decomposition of the organic-transition metal precursor ($M^1L_n$) or the produced scaffold material-transition metal ligand complex ([SM]-$M^1L_{(n-1)}$) may occur. Reaction duration may be from 3 to 50 hours, more preferably from 10 to 30 hours. If the reaction duration is less than 3 hours, decoration of the organic-transition metal precursor ($M^1L_n$) may not undergo completely. If it is more than 50 hours, organic ligand (L) of the organic-transition metal precursor ($M^1L_n$), which is relatively unstable in solvent, may be deformed.

Preferably, organic solvent for purification is oxygen-free (containing no oxygen in the chemical structure) solvent such as (C1-C10) saturated aliphatic hydrocarbon or (C6-C20) aromatic hydrocarbon, for example benzene, chloroform, methylene chloride, toluene, xylene, pentane, hexane or heptane. The solvent may be used alone or as a mixture. Toluene, pentane or their mixture may be more preferably used. In case of using organic solvent containing oxygen in the structural formula, side reaction such as substitution of organic ligand (L) of organic-transition metal precursor ($M^1L_n$) may possibly occur.

The second stage is to apply hydrogen source to the scaffold material-transition metal ligand complex ([SM]-$M^1L_{(n-1)}$) of Chemical Formula (3) to perform hydrogenation, thereby obtaining the SM-transition metal hydride complex ([SM]-$M^1H_{(n-1)}$) of Chemical Formula (1). Depending on the type of hydrogen source, the reaction is carried out in gas or liquid phase. More specifically, the reaction in gas phase is characterized in that the reaction is achieved by applying hydrogen, or a gaseous mixture of hydrogen and at least one type(s) of inert gas to the reaction; while the reaction in liquid phase is characterized in that hydrogen, or a gaseous mixture of hydrogen and at least one type(s) of inert gas is applied to the reaction, but using solvent (used alone or as a mixture), also serving as hydrogen source, selected from (C1-C10) saturated aliphatic hydrocarbons or (C6-C20) aromatic hydrocarbons (such as toluene, benzene, xylene, pentane, hexane and heptanes), which do not contain oxygen in the structural formula.

In case of the reaction in gas phase, scaffold material-transition metal ligand complex ([SM]-$M^1L_{(n-1)}$) of Chemical Formula (3) is loaded to a batch-type or continuous reactor, and reaction is carried out at a temperature range of 25~1000° C., preferably 25~400° C. If reaction temperature is lower than 25° C., hydrogenation cannot be well performed. If it is higher than 1000° C., decomposition of the SM-transition metal linker complex ([SM]-$M^1L_{(n-1)}$) of Chemical Formula (3) and the produced SM-transition metal hydride complex ([SM]-$M^1H_{(n-1)}$) of Chemical Formula (1) would occur.

Reaction pressure is from 1 to 50 atm, preferably from 1 to 20 atm, more preferably from 5 to 15 atm. If it is less than 1 atm, hydrogenation cannot be well performed. If it is more than 50 atm, decomposition of the SM-transition metal ligand complex ([SM]-$M^1L_{(n-1)}$) of Chemical Formula (3) and the produced SM-transition metal hydride complex ([SM]-$M^1H_{(n-1)}$) of Chemical Formula (1) would occur.

Reaction duration is from 1 to 100 hours, preferably from 1 to 50 hours, more preferably from 3 to 10 hours. If it is less than 1 hour, hydrogenation cannot be well performed. If it is more than 100 hours, decomposition of the SM-transition metal ligand complex ([SM]-$M^1L_{(n-1)}$) of Chemical Formula (3) and the produced SM-transition metal hydride complex ([SM]-$M^1H_{(n-1)}$) of Chemical Formula (1) would occur.

The amount of the SM-transition metal ligand complex ([SM]-$M^1L_{(n-1)}$) of Chemical Formula (3) to be loaded, on the basis of the volume of the reactor, is from 0.001 to 1 g/ml, preferably from 0.005 to 0.5 g/ml, more preferably from 0.01 to 0.1 g/ml. If the amount is less than 0.001 g/ml, decomposition of the SM-transition metal linker complex ([SM]-$M^1L_{(n-1)}$) of Chemical Formula (3) and the produced SM-transition metal hydride complex ([SM]-$M^1H_{(n-1)}$) of Chemical Formula (1) would occur. If it is more than 1 g/ml, hydrogenation cannot be well performed.

In case of the reaction in liquid phase, the SM-transition metal ligand complex ([SM]-$M^1L_{(n-1)}$) of Chemical Formula (3) and reaction solvent are loaded to a two-necked round bottomed flask, and the reaction is carried out with flush of hydrogen, or gaseous mixture of hydrogen and at least one type of inert gas at ambient pressure. When the reaction is completed, one or both of the following processes is (are) applied in order to remove the reaction solvent and reaction byproducts, and finally obtain the SM-transition metal hydride complex ([SM]-$M^1H_{(n-1)}$) of Chemical Formula (1):

a) drying in vacuo for 24 hours, more preferably 48 hours with applying Schlenk method in order to remove residual reaction solvent and organic solvent for purification [preferable organic solvent may be employed in purification stage(s)]

b) applying chemical extraction with supercritical $CO_2$ (Korean Patent Application No. 10-2008-0044633).

Reaction temperature in liquid phase is from 25 to 400° C., preferably from 25 to 200° C. If reaction temperature is lower than 25° C., hydrogenation cannot be well performed. If it is higher than 400° C., decomposition of the SM-transition metal ligand complex ([SM]-$M^1L_{(n-1)}$) of Chemical Formula (3) and the produced SM-transition metal hydride complex ([SM]-$M^1H_{(n-1)}$) of Chemical Formula (1) would occur.

Reaction duration is from 1 to 100 hours, preferably from 1 to 50 hours, more preferably from 3 to 24 hours. If it is less than 1 hour, hydrogenation cannot be well performed. If it is more than 100 hours, decomposition of the SM-transition metal linker complex ($[SM]\text{-}M^1L_{(n-1)}$) of Chemical Formula (3) and the produced SM-transition metal hydride complex ($[SM]\text{-}M^1H_{(n-1)}$) of Chemical Formula (1) would occur.

Preferably, organic solvent that is oxygen-free (containing no oxygen in the chemical structure), such as (C1-C10) saturated aliphatic hydrocarbon or (C6-C20) aromatic hydrocarbon, is preferably used alone or as a mixture. Specific examples of such solvent include benzene, chloroform, methylene chloride, toluene, xylene, pentane, hexane and heptane. Solvent having relatively high boiling point, such as toluene, pentane or their mixture may be more preferably used.

In case of using organic solvent containing oxygen in the structural formula, side reaction such as substitution of hydrogen (H) of the SM-transition metal hydride complex ($[SM]\text{-}M^1H_{(n-1)}$) of Chemical Formula (1) may possibly occur, and the solvent is coordinated around the transition metal to decrease hydrogen storage.

The amount of the SM-transition metal ligand complex ($[SM]\text{-}M^1L_{(n-1)}$) of Chemical Formula (3) to be loaded, on the basis of the volume of the reaction solvent, is from 0.0001 to 1 g/ml, preferably from 0.001 to 0.05 g/ml, more preferably from 0.001 to 0.01 g/ml. If the amount is less than 0.0001 g/ml, decomposition of the SM-transition metal ligand complex ($[SM]\text{-}M^1L_{(n-1)}$) of Chemical Formula (3) and the produced SM-transition metal hydride complex ($[SM]\text{-}M^1H_{(n-1)}$) of Chemical Formula (1) would occur. If it is more than 1 g/ml, hydrogenation cannot be well performed.

All the reactions in the first stage and the second stage are carried out in a glove box, on the basis of Schlenk technology under at least one type of inert gas (argon, nitrogen, helium), in order to avoid possible decomposition of the reactants or products.

Fourth aspect of the present invention relates to a scaffold material-transition metal halide complex represented by Chemical Formula (2), which is comprised of scaffold material (SM), and transition metal halide ($M^1X_{(n-1)}$) which is chemically bonded to functional groups formed on the surface of the scaffold material:

$$[SM]\text{-}M^1X_{(n-1)} \qquad \text{[Chemical Formula 2]}$$

wherein, [SM] represents scaffold material containing functional groups on the surface, $M^1$ represents transition metal having the valency of at least 2, X is selected from halogen elements, and n represents the valency of $M^1$.

Fifth aspect of the present invention relates to a process for preparing a scaffold material (SM)-transition metal halide complex, which specifically comprises reacting a scaffold material (SM) containing a functional group formed on the surface with transition metal halide of Chemical Formula (5) to provide bonding of transition metal halide to the functional group, thereby forming the scaffold material (SM)-transition metal halide complex represented by Chemical Formula (2).

$$[SM]\text{-}M^1X_{(n-1)} \qquad \text{[Chemical Formula 2]}$$

$$M^1X_n \qquad \text{[Chemical Formula 5]}$$

wherein, [SM] represents scaffold material containing functional groups on the surface, $M^1$ represents transition metal having the valency of at least 2, X is selected from halogen elements, and n represents the valency of $M^1$.

Inorganic oxides, carbon substances or metal organic frameworks (MOFs) may be used as the scaffold material. The functional groups formed on the scaffold material are reacted with transition metal halide of Chemical Formula (5) to provide linkage of the transition metal to the scaffold material. The functional groups formed on the surface of the scaffold material are selected from a group consisting of —OH, —SH, —COOR$^{21}$, —NH$_2$, —HNR$^{22}$, —NR$^{23}$R$^{24}$, —PH$_2$, —PHR$^{25}$, —PR$^{26}$R$^{27}$, —SO$_3$R$^{28}$, —PO$_3$HR$^{29}$ and —PO$_3$R$^{30}$, wherein R$^{21}$, R$^{28}$ and R$^{29}$ independently represent hydrogen or alkali metal, R$^{22}$ through R$^{27}$ are independently selected from (C1-C20)alkyl, (C3-C8)cycloalkyl, (C6-C20) aryl, (C6-C20)ar(C1-C20)alkyl and (C1-C20)alkyl(C6-C20) aryl group, and R$^{30}$ preferably represents alkaline earth metal.

Depending upon the amount of transition metal halide, all or part(s) of functional groups on the scaffold material may participate in the reaction to remove hydrogen or other leaving group(s) from the functional groups. For example, functional groups such as —OH, —SH, —COOR$^{21}$, —NH$_2$, —HNR$^{22}$, —PH$_2$, —PHR$^{25}$ are converted to —O—, —S—, —COO—, —NH—, —NR$^{22}$—, —PH—, —PR$^{25}$—, respectively, via reaction with transition metal halide.

The scaffold material (SM) containing functional groups on the surface and transition metal halide may be individually incorporated to solvent, and the solution of transition metal halide solution is added to the SM solution to carry out the reaction. One or more solvent selected from a group consisting of tetrahydrofuran, toluene, benzene, dichloromethane and chloroform may be used. It is concerned that transition metal halide may sensitively react with air or moisture to be converted to stable type of metal oxide, so that all synthetic and purifying processes are preferably carried out under inert atmosphere selected from argon, nitrogen or helium, and the solvent is used after purification.

The reaction can be quenched depending upon the status of generation of hydrogen halide (HX) gas at the reaction temperature of –80~120° C., more preferably –30~100° C. The reaction duration may be from 3 to 50 hours, more preferably from 5 to 20 hours, but this is not critically restricted. After preparing the SM-transition metal halide, purification may be carried out by using solvent, specifically toluene, in order to remove the unreacted substances and byproducts. Solvent is removed by using a rotary evaporator or distillation under reduced pressure, and then drying may be carried out. Duration of drying depends upon the type of scaffold material: it is at least 3 hours, more preferably at least 6 hours when the SM is metal organic framework, while it is at least 24 hours, more preferably at least 48 hours when other SM is used, to obtain the SM-transition metal halide.

The process for preparing the SM-transition metal halide complex may include a stage for incorporating functional groups on the surface of SM (such as inorganic oxides or carbon substances), prior to the stage of forming the SM-transition metal halide complex. Functional groups may be incorporated through conventional modification. When the SM is a metal organic framework, a stage for preparing metal-organic framework (MOF) via reaction of organic linker containing function groups which can react with transition metal ($M^1$) halide with metal ion ($M^2$) may be additionally included.

Sixth aspect of the present invention relates to a scaffold material-transition metal ligand complex represented by Chemical Formula (3), which is comprised of scaffold material (SM), and transition metal ligand ($M^1L_{(n-1)}$) which is chemically bonded to the functional groups formed on the surface of SM.

$$[SM]\text{-}M^1L_{(n-1)} \qquad \text{[Chemical Formula 3]}$$

wherein, [SM] represents scaffold material containing functional groups on the surface, $M^1$ represents transition metal having the valency of at least 2, L represents an organic ligand that may be same or different from each other, or may be linked each other to be chelated to metal as a bidentate or tridentate ligand, and n represents the valency of $M^1$.

Seventh aspect of the present invention relates to a process for preparing a scaffold material (SM)-transition metal ligand complex, which comprises reacting a scaffold material (SM) containing functional groups formed on the surface with an organic-transition metal precursor of Chemical Formula (4) to provide linkage of transition metal ligand on the functional group, thereby forming the scaffold material (SM)-transition metal ligand complex represented by Chemical Formula (3).

[SM]-$M^1L_{(n-1)}$            [Chemical Formula 3]

$M^1L_n$            [Chemical Formula 4]

wherein, [SM] represents scaffold material containing functional groups on the surface, $M^1$ represents transition metal having the valency of at least 2, L represents an organic ligand that may be same or different from each other, or may be linked each other to be chelated to metal as a bidentate or tridentate ligand, and n represents the valency of $M^1$.

BEST MODE FOR CARRYING OUT THE INVENTION

Figure 1:
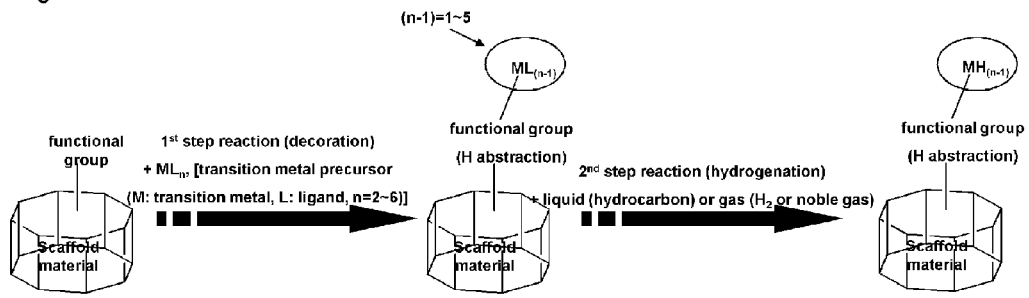
FIG. 1—Schematic diagram of reactions

The present invention is further described by referring to the constitution and effect with regard to preferable embodiments of the invention. It is described in order for persons having ordinary skill in the technical field to which the invention belongs, to easily carry out the invention, not being intended to limit the scope of the invention by any means.

Example 1

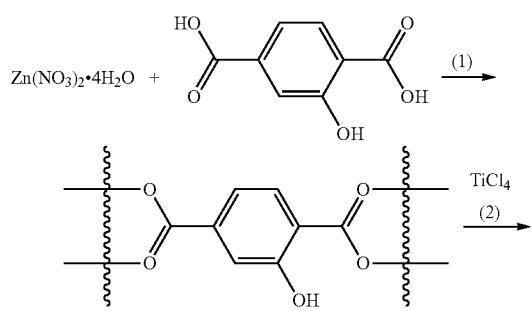

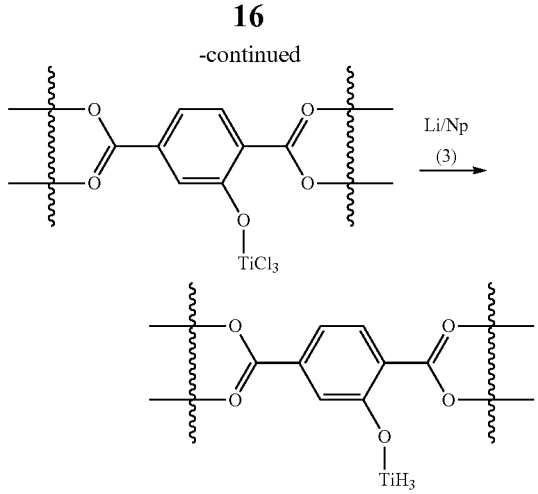

(1) Synthesis of Metal Organic Framework Material (Modified MOF): $Zn_4O(C_8H_4O_5)_3$ In a 250 mL two-necked round bottomed flask, charged were 2-hydroxy-1,4-benzenedicarboxylic acid (4.1 mmol) and zinc nitrate tetrahydrate (11.0 mmol) under nitrogen atmosphere, and the mixture was dissolved in 100 mL of dimethylformamide (DMF). In a closed vessel, the solution was subjected to reaction at 100° C. for 20 hours. Purification by using chloroform and drying under reduced pressure gave metal organic framework containing hydroxyl groups. Yield: 80%. FT-IR: 3400(br). Elemental analysis (EA) (% calc/found): C, 35.2/35.3; H, 1.48/2.00. XRF (% calc/found): Zn, 32.0/30.8.

(2) Synthesis of Metal Organic Framework-Transition Metal Halide Complex [SM: Metal Organic Framework, Product: $Zn_4O(C_8H_3O_5TiCl_3)_3$]

In a two-necked flask (250 mL) equipped with a magnetic stirrer and a condenser, charged were metal organic framework material (4 mmol) containing hydroxyl groups [prepared from stage (1)] and toluene (50 mL) under nitrogen atmosphere. Solution of $TiCl_4$ (1M) in toluene (13 mL) was slowly added dropwise thereto. Upon adding the solution, color of the mixture immediately changed to dark red with discharging HCl gas. The reaction was continued at 30° C. for 5 hours, while hydrogen chloride gas generated during the synthesis was neutralized by using aqueous ammonium solution. After confirming the completion of reaction by hydrogen chloride cloud generated, the solvent was removed under reduced pressure to dryness. Entire reaction was carried out under Ar or $N_2$ atmosphere in order to avoid contact with air. Any organic solvent used was anhydrous grade. Yield: 85%. Elemental analysis (EA) (% calc/found): C, 22.6/23.8; H, 0.71/1.03. XRF (% calc/found): Zn, 20.5/21.6; Ti, 11.2/9.05.

(3) Preparation of Metal Organic Framework-Transition Metal Hydride Complex [SM: Metal Organic Framework $Zn_4O(C8H_6O_5Ti)_3$]

In a two-necked flask (250 mL) equipped with a magnetic stirrer and a condensor, Li metal (4.86 mmol) and naphthalene (4.86 mmol) were dissolved in 70 mL of DME (1,2-dimethoxyethane) under argon atmosphere. The solution was activated for about 10 hours so that interaction between Li metal and naphthalene occurs sufficiently. The metal organic framework-transition metal halide complex (1.6 mmol) prepared from stage (2) was charged thereto, and the mixture stirred at room temperature for 24 hours or more. Since the reaction product, metal organic framework-transition metal hydride, is bonded to the metal-organic framework material, it remains as solid on the bottom of the flask. Byproducts resulted from the reaction are classified as organic substances and inorganic substances. Tetrahydrofuran as polar solvent was used for purification in order to remove LiCl as inorganic byproduct, and pentane solution was used to completely remove naphthalene derivatives as organic byproducts. Finally, the residual solvent in the resultant product was removed under reduced pressure, and the product dried to obtain pure metal organic framework-transition metal hydride material. Likewise the synthesis of the precursor, entire reaction was carried out under Ar atmosphere to avoid contact with air, and any organic solvent used was anhydrous grade. Yield: 85%. Elemental analysis (EA) (% calc/found): C, 29.8/31.2; H, 1.88/2.15. XRF (% calc/found): Zn, 27.0/28.4; Ti, 14.8/12.4.

Example 2

(1) Preparation of Multiwall Carbon Nanotube (MWCNT)-[O,COO]-transition metal Halide Complex [SM: Multiwall Carbon Nanotubes Containing —OH Groups and —COOH Groups on the Surface (—OH & —COOH Groups: 6 wt %)

Multiwall carbon nanotubes containing —OH groups and —COOH groups on the surface (—OH & —COOH groups: 6 wt %) can be prepared by applying various processes for surface modification proposed by Korean Patent No. 10-2008-0117106. The present example is prepared by applying one of them. Specific description is given below.

Multiwall carbon nanotubes (12 g) (referred to as MWCNT hereinbelow)(trade name: CM95, from Hanwha Nanotech) was mixed with distilled water (988 g) by using a circulation pump to prepare MWCNT solution in a pretreatment vessel. Before incorporating the MWCNT solution to a preheating vessel at a flow rate of 30 g/min through high pressure injection pump, the MWCNT solution was mixed with compressed gaseous oxygen at 245 atm ~252 atm via shear of a heat exchanger at a flow rate of 0.8 g/min, and the mixture was incorporated to the preheating vessel preheated at 200~260° C. The preheated mixture was injected to a reactor for surface modification in sub-critical water state at 350° C. and 230~250 atm to undergo surface modification. The surface modified product was transported back to the heat exchanger, and subjected to first cooling to 200° C., and then cooled to about 25° C. via a cooling device, to obtain 11.8 g of MWCNT that had been continuously surface modified.

To a two-necked round-bottomed flask (250 mL), charged were the surface modified MWCNT (0.5 g) and toluene (100 mL) under argon atmosphere to prepare Reactant A. In a one-necked round-bottomed flask (250 mL), 1M $TiCl_4$ (solvent: toluene) (4.125 mL) was dissolved in 30 mL of toluene to prepare Reactant B. After stirring Reactant A for 1 hour, Reactant B was slowly added dropwise thereto, and the mixture was heated under reflux at 50° C. for 24 hours. Under argon atmosphere, toluene as reaction solvent was removed under reduced pressure, and unreacted $TiCl_4$ was filtered off by using toluene as purification solvent. Removal of the purification solvent under reduced pressure gave Product A. Yield: 98%. Anal. Calc. (XRF, EA): Ti, 10.18; C, 58.07; O, 3.92; H, 0%. Anal. Found (XRF, EA): Ti, 10.50; C, 56.07; O, 4.02; H, 0.5.

In order to elucidate possibility of disintegration of structure of multiwall carbon nanotubes by $TiCl_4$ (a strong reductant), SEM, XRD and Raman analyses were performed. As the results, it was found that inherent morphology and crystalline structure of MWCNT were maintained after the reaction.

As the result of IC analysis to elucidate amount of Cl being present in Product A, atomic ratio of Ti to Cl was 1:2.4, which means $TiCl_2$ or $TiCl_3$ is well grafted on the functional groups existing on the surface of MWCNT.

(2) Preparation of MWCNT-[O,COO]-Transition Metal Hydride Complex [SM: Multiwall Carbon Nanotubes Containing —OH Groups and —COOH Groups on the Surface (—OH & —COOH Groups: 6 wt %)

To a three-necked round-bottomed flask (250 mL), charged were Product A (0.5 g, Cl⁻ 7.06 mmol) was dissolved in DME (50 mL) under argon atmosphere to prepare Reactant C. In a one-necked round-bottomed flask (100 mL), Li (0.049 g, 7.06 mmol) and naphthalene (0.995 g, 7.7 mmol) were added to 30 mL of DME under argon atmosphere to prepare Reactant D. After 10 hours, Reactant D was slowly added dropwise to Reactant C, and the mixture was set under reflux at 10° C. for 24 hours. Under argon atmosphere, DME as reaction solvent was removed under reduced pressure, and unreacted substances and reaction byproducts were removed by using toluene as purification solvent. Removal of solvent under reduced pressure gave Product B. Yield: 95%. Anal. Calc. (XRF, EA): Ti, 13.3; C, 65.07; O, 4.89; H, 0.1%. Anal. Found (XRF, EA): Ti, 14.2; C, 66.91; O, 4.55; H, 0.3.

For total elucidation of Product B and the byproducts, SEM, XRD, Raman, IC, SEM and ESR (Electron Spin Resonance Spectrometer) were performed, and the analytical results are described below.

As the result of SEM, XRD and Raman analysis, it was found that LiCl was formed as byproduct, and inherent morphology and crystalline structure of MWCNT were maintained after formation of Product B. As the result of separation and purification using toluene, it was found that most of LiCl was purified. In order to more specifically elucidate LiCl and unreacted substances that may be present in Product B in a trace amount, IC analysis was performed, and about 2.3% of LiCl was found to be present in the product. As the result of ESR analysis of the product, oxidation number of Ti was +4.

Figure 2:
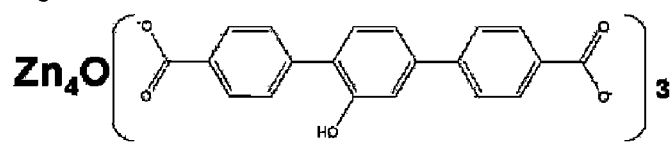
FIG. 2—Base unit of Zn-containing MOF (1274.57 g/B.U.)

In Examples 3 to 5, employed were mesoporous silica and Zn-containing MOF (FIG. 2), which is characterized in that 1) transition metal hydride bondings decorated on the SM are present having the distance that avoids aggregation each other, 2) physicochemical stability is excellent, and 3) solubility in hydrocarbon solvent is low enough to be separated and purified.

Example 3

(1) Preparation of mesoporous silica-O-transition metal halide complex [SM: Mesoporous Silica Containing —OH Groups on the Surface (—OH Group 1 mmol/g)]

In a two-necked round-bottomed flask (250 mL), mesoporous silica containing —OH groups on the surface (—OH group 1 mmol/g) (XPO-2410 from GRACE DAVISON) (0.5 g) was added to 50 ml toluene under argon atmosphere to prepare Reactant E. In a one-necked round-bottomed flask (100 mL), 1M TiCl$_4$ (solvent: toluene) (1.3 mL) was dissolved in 30 mL of toluene to prepare Reactant F. After stirring Reactant E for 1 hour, Reactant F was slowly added dropwise thereto, and the mixture was heated under reflux at 50° C. for 18 hours. Under argon atmosphere, toluene as reaction solvent was removed under reduced pressure, and unreacted TiCl$_4$ was filtered off by using toluene. Removal of toluene under reduced pressure gave Product C. Yield: 99%. Anal. Calc. (XRF): Si, 47.76; Ti, 4.15. Anal. Found (XRF): Si, 46.73; Ti, 4.57%.

As the result of elemental analysis (EA) of Product C thus prepared, trace amount of C, H and N was detected. This means no significant amount of reaction solvent or purification solvent exists in Product C. In order to elucidate possibility of disintegration of silica structure by TiCl$_4$, a strong reductant, SEM (scanning electron microscope) and XRD (X-ray diffraction) were performed. As the result, it was found that inherent morphology and crystalline structure of silica were maintained. As the result of IC analysis to elucidate amount of Cl being present in Product C, atomic ratio of Ti to Cl was 1:2.89, which means TiCl$_3$ is well grafted on the functional groups existing on the surface of silica.

(2) Preparation of Mesoporous Silica-O-Transition Metal Hydride Complex [SM: Mesoporous Silica Containing —OH Groups on the Surface (—OH Group 1 mmol/g)]

In a three-necked round-bottomed flask (250 mL), Product C (0.5 g, 3 mmol based on Cl) was dissolved in DME (50 mL) under argon atmosphere to prepare Reactant G.

In a one-necked round-bottomed flask (100 mL), Li (0.011 g, 9 mmol) and naphthalene (0.212 g, 9.9 mmol) were added to 30 mL of DME under argon atmosphere to prepare Reactant H. After 10 hours, Reactant H was slowly added dropwise to Reactant G, and the mixture was set under reflux at 10° C. for 18 hours. Under argon atmosphere, DME as reaction solvent was removed under reduced pressure, and unreacted substances and reaction byproducts were removed by using toluene as purification solvent. Removal of solvent by employing Schlenk method gave Product D. Yield: 96%. Anal. Calc. (XRF): Si, 52.46; Ti, 4.56. Anal. Found (XRF): Si, 51.13; Ti, 4.28%.

For total elucidation of Product D and the byproducts, SEM, XRD, IC and ESR (Electron Spin Resonance Spectrometer) analyses were performed, and the analytical results are described below.

As the result of SEM and XRD analysis, it was found that LiCl was formed as byproduct, and inherent morphology and crystalline structure of silica were maintained after formation of Product D. As the result of XRD analysis after separation and purification using toluene, it was found that most of LiCl was purified. In order to more specifically elucidate LiCl and unreacted substances that may be present in the product in a trace amount, IC analysis was performed, and about 1.3% of LiCl was found to be present in Product D. As the result of ESR (Electron Spin Resonance Spectrometer) of Product D, oxidation number of Ti was +4.

Example 4

(1) Preparation of Mesoporous Silica-O-Transition Metal Ligand Complex [SM: Mesoporous Silica Containing —OH Groups on the Surface (—OH Group 1 mmol/g, Grace-Davison)]

Figure 3:
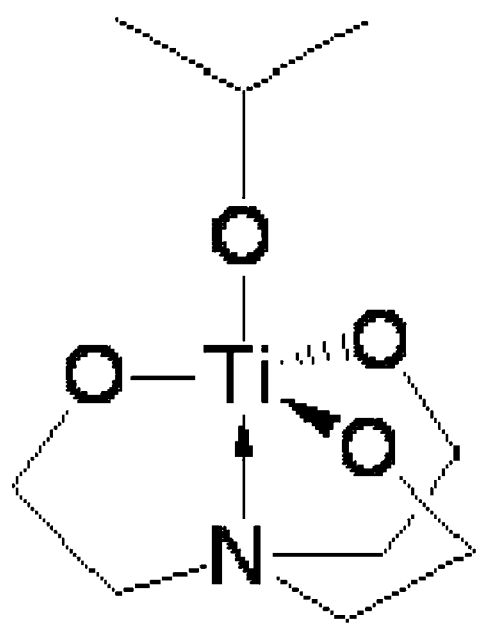
FIG. 3 organic-transition metal precursor (isopropoxytitanatrane) of Example 4

In a two-necked round-bottomed flask (250 mL), mesoporous silica containing —OH groups on the surface (—OH group 1 mmol/g) (XPO-2410, from GRACE DAVISON) (0.5 g) was dispersed in 50 mL of toluene under argon atmosphere to prepare Reactant I. In a one-necked round-bottomed flask (100 mL), isopropoxytitanatrane (FIG. 3) (5 mmol) was dissolved in 30 mL of toluene to prepare Reactant J. After stirring Reactant I for 1 hour, Reactant J was slowly added dropwise thereto, and the mixture was set under reflux at 25° C. for 18 hours. Under argon atmosphere, toluene as reaction solvent was removed by Schlenk method, and unreacted isopropoxytitanatrane was filtered off by using toluene as purification solvent. Removal of toluene (used as reaction solvent and organic solvent for purification) by Schlenk method gave Product E. Yield: 99%. Anal. Calc. (XRF): Si, 46.17; Ti, 4.01. Anal. Found (XRF): Si, 46.14; Ti, 3.81%. Anal. Calc. (EA): C, 6.04; H, 0.92; N, 1.17%. Anal. Found (EA): C, 6.50; H, 1.13; N, 1.12. %.

Figure 4:
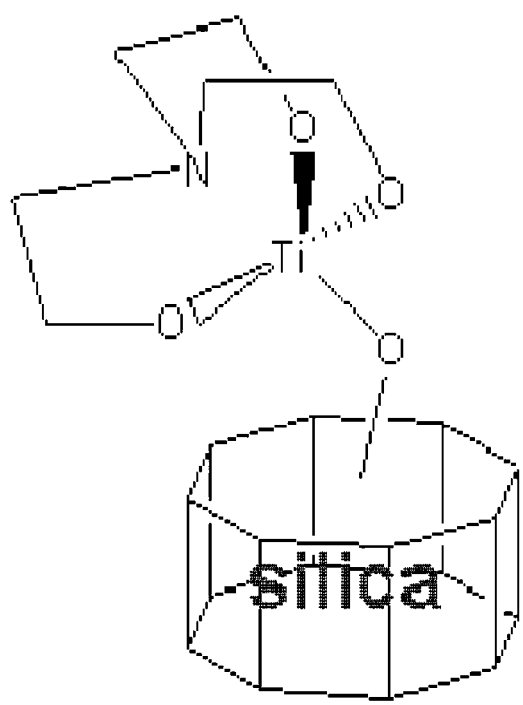
FIG. 4—Product E of Example 4

As the result of $^1$H-NMR (solution in CDCl$_3$) analysis of Product E thus prepared, only trace amount of toluene (used as reaction solvent and purification solvent) was detected. This means unreacted substances are not present in the product. In order to elucidate possibility of disintegration of silica structure by isopropoxytitanatrane, SEM (scanning electron microscope) and XRD (X-ray diffraction) analyses were performed. As the results, it was found that inherent morphology and crystalline structure of silica were maintained. In order to elucidate completion of the reaction, IR analysis was performed. As the result, it was found that the peak at 3880 cm$^{-1}$ (—OH groups of silica) disappeared when the reaction was completed. On the basis of content analysis (XRF, EA) and IR analysis, it was found that Product E has the structure shown in FIG. 4.

Figure 7:
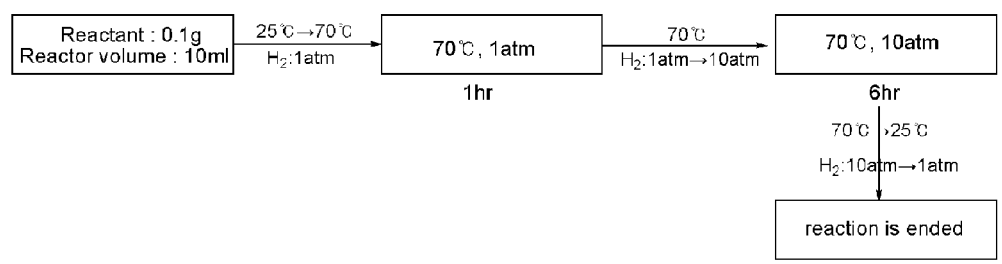
FIG. 7—Reaction diagram of 2-stage hydrogenation of Example 4

(2) Preparation of Mesoporous Silica-O-Transition Metal Hydride Complex [SM: Mesoporous Silica Containing —OH Groups on the Surface (—OH Group 1 mmol/g. Grace-Davison)] [Reaction in Gas Phase. FIG. 7]

To a continuous type reactor (reactor volume: 10 ml), Product E (0.1 g) was loaded, and the temperature inside the reactor was raised to 70° C. and maintained for 1 hour, while flushing hydrogen gas at ambient pressure. After one hour, hydrogen pressure inside the reactor was raised to 10 atm, which was then maintained for 6 hours. After 6 hours, the hydrogen pressure was altered to ambient pressure, and temperature inside the reactor to ambient temperature. The reaction was quenched to obtain Product F. Yield: 98.5%. Anal. Calc. (XRF): Si, 52.46; Ti, 4.56. Anal. Found (XRF): Si, 51.13; Ti, 4.28%.

For total elucidation of Product F and the byproducts, GC-MASS, SEM, XRD, ESR (Electron Spin Resonance Spectrometer) and EA analyses were performed, and the analytical results are described below.

As the result of GC-MASS, it was found that triethanolamine was produced as byproduct of hydrogenation. As the result of SEM and XRD analysis, it was found that inherent morphology and crystalline structure of silica were maintained, but no crystalline structure of Ti (metal) or TiO$_x$ type was observed. This means TiH$_3$ was not aggregated, but very well decorated on silica in atomic-scale. As the result of ESR of Product F, oxidation number of Ti was +4. As the result of EA analysis of Product F [C (0.05 wt %), H (0.25 wt %) and N (0.01 wt %), it was found that hydrogenation was perfectly occurred, but significantly no triethanolamine was present in Product F as the reaction byproduct.

Example 5

(1) Preparation of Metal Organic Framework-O-Transition Metal Ligand Complex [SM: MOF Containing —OH Groups on the Surface (Zn-Containing-MOF, $Zn_4O(C_{20}H_{12}O_5)_3$, —OH Group) (FIG. 2)]

Figure 5:
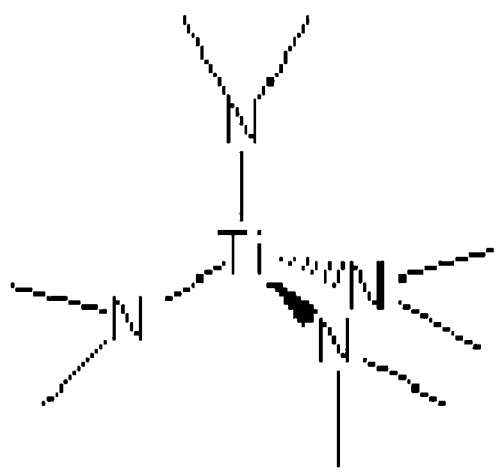
FIG. 5 organic-transition metal precursor (tetrakisdimethylaminotitanium) of Example 5

In a one-necked round-bottomed flask (50 mL), Zn-containing MOF (0.1 g) was dispersed in 20 mL of toluene under argon atmosphere to prepare Reactant K. In a one-necked round-bottomed flask (100 mL), tetrakisdimethylaminotitanium ($Ti(NMe_2)_4$) (FIG. 5) (0.24 mmol) was dissolved in 20 mL of toluene to prepare Reactant L. Reactant L was slowly added dropwise to Reactant K, and the mixture stood at 25° C. for 24 hours, and the reaction was quenched. By employing chemical extraction process with supercritical $CO_2$ (50° C., 200 bar, 3 hr) (Korean Patent No. 10-2009-0044633), reaction solvent and unreacted substances were removed to obtain Product G. Yield: 98%. Anal. Calc. (XRF): Zn, 15.59; Ti, 8.56. Anal. Found (XRF): Zn, 15.51; Ti, 8.37%. Anal. Calc. (EA): C, 51.48; H, 4.11; N, 5.01%. Anal. Found (EA): C, 50.11; H, 4.78; N, 4.62%.

Figure 6:
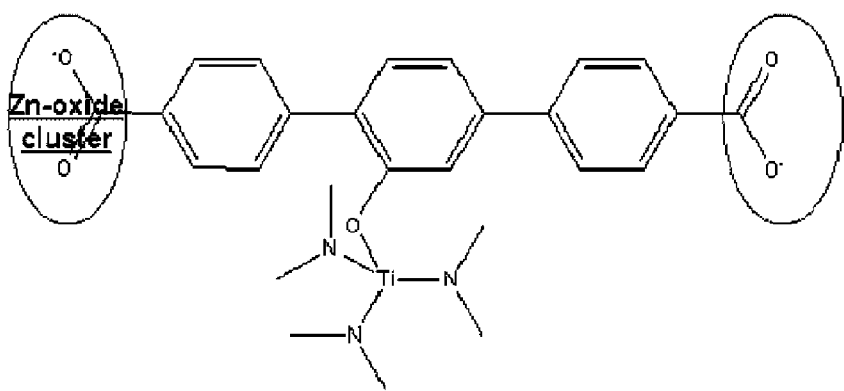
FIG. 6—Product G of Example 5

As the result of $^1$H-NMR (solution in $CDCl_3$) of Product G thus prepared, only trace amount of $CDCl_3$ (used as solvent for NMR) was detected. This means unreacted substances are not present in the product. Further, according to the same analytical result, no peak of organic ligand was detected. This means tetrakisdimethyllaminotitanium did not disintegrate the structure of Zn-containing MOF. In order to additionally elucidate possibility of disintegration of Zn-containing MOF by tetrakisdimethylaminotitanium, SEM (scanning electron microscope) and XRD (X-ray diffraction) were performed. As the result, it was found that inherent morphology and crystalline structure of Zn-containing MOF were maintained even after the reaction. In order to elucidate completion of the reaction, IR analysis was performed. As the result, it was found that the peak at 3750 cm$^{-1}$ (—OH group of Zn-containing MOF) disappeared when the reaction was completed. On the basis of content analysis (XRF, EA) and IR analysis, it was found that Product G has the structure shown in FIG. 6.

(2) Preparation of MOF-O-Transition Metal Hydride Complex [SM: MOF Containing —OH Groups on the Surface (Zn-Containing MOF, $Zn_4O(C_{20}H_{12}O_5)_3$, —OH Group) (FIG. 2)] [Reaction in Liquid Phase]

To a two-necked round-bottomed flask (reactor volume: 250 ml), Product G (0.1 g) and 50 mL of toluene were charged, and gaseous mixture of hydrogen/argon was flushed under ambient pressure. The temperature inside the reactor was then raised to 100° C. and maintained for 10 hours. Then temperature inside the reactor was altered to ambient temperature, and the reaction was quenched. By employing chemical extraction process with supercritical $CO_2$ (50° C., 200 bar, 2 hr) (Korean Patent No. 10-2009-0044633), reaction solvent and unreacted substances were removed to obtain Product H. Yield: 98%. Anal. Calc. (XRF): Zn, 18.38; Ti, 10.09. Anal. Found (XRF): Zn, 18.11; Ti, 9.97%. Anal. Calc. (EA): C, 50.59; H, 2.95; N, 0%. Anal. Found (EA): C, 50.09; H, 3.11; N, 0.08%.

For total elucidation of Product H and the byproducts, GC-MASS, SEM, XRD, ESR and EA analyses were performed, and the analytical results are described below.

As the result of GC-MASS, it was found that dimethylamine was produced as byproduct of hydrogenation. As the result of SEM and XRD analysis, it was found that inherent morphology and crystalline structure of Zn-containing MOF were maintained, but no crystalline structure of Ti (metal) or $TiO_x$ type was observed. This means $TiH_3$ was not aggregated, but very well decorated on Zn-containing MOF in atomic-scale. As the result of ESR analysis of Product H, oxidation number of Ti was +4. As the result of EA analysis of Product H, it was found that Product H has elemental contents being approximate to the theoretical value. This means hydrogenation was almost perfectly performed, but significantly no dimethylamine as the reaction byproduct was present in Product H.

Example 6

(1) Preparation of Mesoporous Silica-O-Transition Metal Ligand Complex [SM: Mesoporous Silica Containing —OH Groups on the Surface (1 mmol/g. Grace-Davison)

Figure 8:
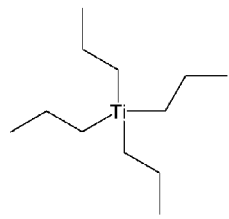
FIG. 8 organic-transition metal precursor (tetrapropyltitanium) of Example 6

In a two-necked round-bottomed flask (250 mL), mesoporous silica containing —OH groups on the surface (—OH group 1 mmol/g, XPO-2410 from Grace Davison) (0.5 g) was dispersed in 50 mL of benzene under argon atmosphere to prepare Reactant M. In a one-necked round-bottomed flask (100 mL), tetrapropyltitanium (FIG. 8) (5 mmol) was dissolved in 30 mL of benzene to prepare Reactant N. Reactant M was stirred for 1 hour, and then Reactant N is slowly dropped to Reactant M, with reflux at 25° C. for 20 hours. Under argon atmosphere, benzene was removed via Schlenk method, and benzene as reaction solvent was applied as organic solvent for purification to filter off unreacted tetrapropyltitanium. Then, benzene as solvent for reaction and purification was removed via Schlenk method to obtain Product I.

Yield: 98%. Anal. Calc. (XRF): Si, 46.80; Ti, 4.07. Anal. Found (XRF): Si, 46.52; Ti, 4.11%. Anal. Calc. (EA): C, 9.18; H, 1.70; N, 0%. Anal. Found (EA): C, 9.03; H, 1.17; N, 0.03. %.

Figure 9:
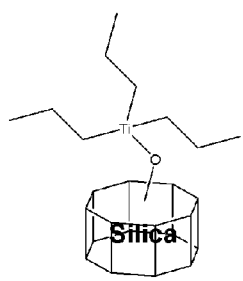
FIG. 9—Product I of Example 6

As the result of $^1$H-NMR (solution in $CDCl_3$) of Product I thus prepared, only trace amount of benzene (used as solvent for reaction and purification) was detected. This means unreacted substances are not present in the product. In order to elucidate possibility of disintegration of the silica structure by tetrapropyltitanium, SEM (scanning electron microscope) and XRD (X-ray diffraction) analyses were performed. As the result, it was found that inherent morphology and crystalline structure of silica were maintained even after the reaction. In order to elucidate completion of the reaction, IR analysis was performed. As the result, it was found that the peak at 3880 cm$^{-1}$ (—OH group of silica) disappeared when the reaction was completed. On the basis of content analysis (XRF, EA) and IR analysis, it was found that Product I has the structure shown in FIG. 9.

(2) Preparation of Mesoporous Silica-O-Transition Metal Hydride Complex [SM: Mesoporous Silica Containing —OH Groups on the Surface (1 mmol/g, Grace-Davison)

[Reaction in Gaseous Phase]

To a continuos reactor (reactor volume: 10 ml), Product I (0.13 g) was loaded, and hydrogen gas was flushed under ambient pressure. The temperature inside the reactor was then raised to 400° C. and maintained for 1 hour. Then, hydrogen pressure inside the reactor was raised to 10 atm, which was maintained for 5.5 hours. Thereafter, hydrogen pressure inside the reactor was altered to ambient pressure, and temperature inside the reactor to ambient temperature. The reaction was quenched to obtain Product J.

Yield: 99.5%. Anal. Calc. (XRF): Si, 52.46; Ti, 4.56. Anal. Found (XRF): Si, 51.01; Ti, 4.11%.

For total elucidation of Product J and the byproducts, GC-MASS, SEM, XRD, ESR (Electron Spin Resonance Spectrometer) and EA analyses were performed, and the analytical results are described below.

As the result of GC-MASS, it was found that propane gas was produced as byproduct of hydrogenation. As the result of SEM and XRD analysis, it was found that inherent morphology and crystalline structure of silica were maintained, but no crystalline structure of Ti (metal) or $TiO_x$ type was observed. This means $TiH_3$ was not aggregated, but very well decorated on silica in atomic-scale. As the result of ESR analysis of Product J, oxidation number of Ti was +4. On the basis of EA analysis of Product J [C (0.01 wt %), H (0.00 wt %) and N (0.02 wt %)], it was found that hydrogenation was almost perfectly performed, but significantly no propane gas as the reaction byproduct was present in Product J.

INDUSTRIAL APPLICABILITY

The present invention relates to substances which can be applied to the technical field of gas storage, polymerization catalysts and optical isomers, their intermediates, and processes for preparing the same. The SM-transition metal hydride complex prepared according to the process for the preparation according to the present invention is advantageous in that 1) possible disintegration of structure of the scaffold material (SM) is impeded, and 2) the process is achieved by relatively simple manufacturing system.

The SM-transition metal hydride complex prepared according to the invention overcomes the problem of decrease of hydrogen storage due to spontaneous aggregation which is resulted from insufficient chemical stability of conventional organic-transition metal hydride complexes. It is thought that such an advantage of SM-transition metal hydride complex of the invention comes from constant distance of each transition metal hydride bonded to the scaffold material.

The SM transition metal hydride complex according to the invention enables hydrogen storage of high capacity and high efficiency due to Kubas binding with hydrogen molecules. Further, avoided can be aggregation of metals themselves or disintegration of structure (such as polymerization with metal through organic ligand) even with repeated adsorption/desorption.

By using chemically stable scaffold material having porosity, physical adsorption of hydrogen due to relatively large surface area can be additionally expected. The structure of scaffold material would not be disintegrated under relatively harsh oxidative or reductive conditions.

The invention claimed is:

1. A scaffold material-transition metal hydride complex represented by Chemical Formula (1), which is comprised of scaffold material (SM), and transition metal hydride ($M^1 H_{(n-1)}$) which is chemically bonded to functional groups formed on the surface of the scaffold material:

$$[SM]-M^1H_{(n-1)} \quad \text{[Chemical Formula 1]}$$

wherein [SM] represents scaffold material containing functional groups on the surface, $M^1$ represents transition metal having the valency of at least 2, and n represents the valency of $M^1$, and wherein the scaffold material is carbon substance or metal organic framework (MOFs).

2. The scaffold material-transition metal hydride complex according to claim 1, wherein the functional group is one or more group(s) selected from a group consisting of —OH, —SH, —COOR$^{21}$, —NH$_2$, —HNR$^{22}$, —NR$^{23}$R$^{24}$, —PH$_2$, —PHR$^{25}$, —PR$^{26}$R$^{27}$, —SO$_3$R$^{28}$, —PO$_3$HR$^{29}$ and —PO$_3$R$^{30}$, R$^{21}$, R$^{28}$ and R$^{29}$ independently represent hydrogen or alkali metal, R$^{22}$ through R$^{27}$ are independently selected from (C1-C20)alkyl, (C3-C8)cycloalkyl, (C6-C20)aryl, (C6-C20)ar(C1-C20)alkyl and (C1-C20)alkyl(C6-C20)aryl group, and R$^{30}$ represents alkaline earth metal.

3. The scaffold material-transition metal hydride complex according to claim 1, wherein the carbon substance is selected from a group consisting of carbon nanotubes (CNT), graphite, carbon nanofiber, carbon nanohorn, fullerence and mixtures thereof.

4. The scaffold material-transition metal hydride complex according to claim 1, wherein the metal organic framework (MOF) comprises metal ($M^2$) and organic linkers ($L^1$) as the framework.

5. The scaffold material-transition metal hydride complex according to claim 4, wherein the organic linker ($L^1$) is selected from the compounds represented by Chemical Formula (7) which contain a functional group ($G^1$) to be linked to the metal ($M^2$) ion in the metal organic framework and a functional group ($G^2$) to be linked to the transition metal hydride ($M^1 H_{(n-1)}$):

$$(G^1)_n\text{-A-}(G^2)_b \quad \text{[Chemical Formula 7]}$$

wherein, A is selected from (C1-C20)alkylene, (C3-C8) cycloalkylene, (C6-C20)arylene, (C6-C20)ar(C1-C20) alkylene, (C1-C20)alkyl(C6-C20)arylene and (C8-C20) fused ring; the (C2-C20)alkylene may comprise unsaturated bonds, carbon atoms of the arylene and alkylene may be replaced by heteroatoms selected from N, O, S and Si, and the arylene and alkylene may be further substituted by a substituent selected from —(CO)R$^{31}$, —(SO$_2$)R$^{32}$, —(CO$_2$)R$^{33}$, —SR$^{34}$, —NO$_2$, —Si(R$^{35}$) (R$^{36}$)(R$^{37}$) and —BR$^{38}$;

$G^1$ represents carboxylate (—COO—), a is an integer from 2 to 4;

$G^2$ is selected from a group consisting of —OH, —SH, —COOR$^{41}$, —NH$_2$, —NHR$^{42}$, —NR$^{43}$R$^{44}$, —PH$_2$, —PHR$^{45}$, —PR$^{46}$R$^{47}$, —SO$_3$R$^{48}$, —PO$_3$HR$^{49}$ and —PO$_3$R$^{50}$, b is an integer from 1 to 15;

R$^{31}$ through R$^{38}$ and R$^{42}$ through R$^{47}$ are independently selected from (C1-C20)alkyl, (C3-C8)cyclo alkyl, (C6-C20)aryl, (C6-C20)ar(C1-C20)alkyl and (C1-C20)alkyl (C6-C20)aryl, R$^{41}$, R$^{48}$ and R$^{49}$ independently represent hydrogen or alkali metal, and R$^{50}$ represents alkaline earth metal.

6. The scaffold material-transition metal hydride complex according to claim 5, wherein A of Chemical Formula (7) is selected from phenylene, naphthylene, biphenylene, terphenylene, anthrylene, py-nylene and perylenylene, which may be further substituted by a substituent selected from —(CO) R$^{31}$, —(SO$_2$)R$^{32}$, —(CO$_2$)R$^{33}$, —SR$^{34}$, —NO$_2$, —Si(R$^{35}$) (R$^{36}$)(R$^{37}$) and —BR$^{38}$; R$^{31}$ through R$^{38}$ are independently selected from (C1-C20)alkyl, (C3-C8)cycloalkyl, (C6-C20) aryl, (C6-C20)ar(C1-C20)alkyl and (C1-C20)alkyl(C6-C20) aryl; a is an integer of 2 or 3, and b is an integer from 1 to 10.

7. The scaffold material-transition metal hydride complex according to claim 4, wherein the metal ($M^2$) is selected from Li$^+$, Na$^+$, K$^+$, Rb$^+$, Be$^{2+}$, Mg$^{2+}$, Ca$^{2+}$, Sr$^{2+}$, Ba$^{2+}$, Sc$^{3+}$, Y$^{3+}$, Ti$^{4+}$, Zr$^{4+}$, Hf$^+$, V$^{4+}$, V$^{3+}$, V$^{2+}$, Nb$^{3+}$, Ta$^{3+}$, Cr$^{3+}$, Mo$^{3+}$, W$^{3+}$, Mn$^{3+}$, Mn$^{2+}$, Re$^{3+}$, Re$^{2+}$, Fe$^{3+}$, Fe$^{2+}$, Ru$^{3+}$, Ru$^{2+}$, Os$^{3+}$, Os$^{2+}$, Co$^{3+}$, Co$^{2+}$, Rh$^{2+}$, Rh$^+$, Ir$^{2+}$, Ir$^+$, Ni$^{2+}$, Ni$^+$, Pd$^{2+}$, Pd$^+$, Pt$^{2+}$, Pt$^+$, Cu$^{2+}$, Cu$^+$, Ag$^+$, Au$^+$, Zn$^{2+}$, Cd$^{2+}$, Hg$^{2+}$, Al$^{3+}$, Ga$^{3+}$, In$^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^{+}$, $Sb^{5+}$, $Sb^{3+}$, $Sb^{+}$, $Bi^{5+}$, $Bi^{3+}$ and $Bi^{+}$.

8. The scaffold material-transition metal hydride complex according to claim 1, wherein the transition metal ($M^1$) is selected from titanium (Ti), vanadium (V) and scandium (Sc).

9. A process for preparing a scaffold material-transition metal hydride complex represented by Chemical Formula (1) via hydrogenation-dehalogenation from a scaffold material-transition metal halide complex (Chemical Formula 2) comprised of scaffold material (SM) and transition metal halide ($M^1X_{(n-1)}$) which is chemically bonded to functional groups formed on the surface of the scaffold material:

[SM]-$M^1H_{(n-1)}$                                     [Chemical Formula 1]

[SM]-$M^1X_{(n-1)}$                                   [Chemical Formula 2]

wherein, [SM] represents scaffold material containing functional groups on the surface, $M^1$ represents transition metal having the valency of at least 2, X is selected from halogen elements, and n represents the valency of $M^1$.

10. A process for preparing a scaffold material (SM)-transition metal hydride complex which is characterized in that
1) a scaffold material (SM) containing a functional group formed on the surface is reacted with an organic-transition metal precursor of Chemical Formula (4) to obtain a SM-transition metal ligand complex having the structure of Chemical Formula (3) wherein the transition metal ligand is linked to the functional groups; and
2) the SM-transition metal ligand complex is then subjected to hydrogenation to provide a SM-transition metal hydride complex having the structure of Chemical Formula (1):

[SM]-$M^1H_{(n-1)}$                                     [Chemical Formula 1]

[SM]-$M^1L_{(n-1)}$                                   [Chemical Formula 3]

$M^1L_n$                                                                           [Chemical Formula 4]

wherein, [SM] represents scaffold material containing functional groups on the surface, $M^1$ represents transition metal having the valency of at least 2, L represents an organic ligand that may be same or different from each other, or may be linked to each other to be chelated to metal as a bidentate or tridentate ligand, and n represents the valency of $M^1$, and wherein the organic ligand (L) is alkyl-type ligand, atrane-type ligand, amino-type ligand oxy-type ligand, thio-type ligand or phosphino-type ligand, which is selected from $Z-(W-Y)_3{}^{3-}$, $-NH_2$, $-NHR^1$, $-NR^1R^2$, $-OH$, $-OR^3$, $-SH$, $-SR^4$, $-PH_2$, $-PHR^5$, $-PR^5R^6$ and $-(CR^7R^8)_yR^9$; Z represents B, $CR^{10}$, N, SH or N; $R^{10}$ represents hydrogen, (C1-C20)alkyl, (C3-C8)cycloalkyl, (C6-C20)aryl, (C6-C20)ar(C1-C20)alkyl or (C1-C20)alkyl(C6-C20)aryl; W represents (C1-C20)alkylene, (C3-C8)cycloalkylene, (C6-C20)arylene, (C6-C20)ar(C1-C20)alkylene or (C1-C20)alkyl(C6-C20)arylene; Y represents $NH_2$, O or S; $R^1$ through $R^6$ independently represent (C1-C20)alkyl, (C3-C8)cycloalkyl, (C6-C20)aryl, (C6-C20)ar(C1-C20)alkyl or (C1-C20)alkyl(C6-C20)aryl; $R^7$ through $R^9$ independently represent hydrogen, (C1-C20)alkyl, (C3-C8)cycloalkyl, (C6-C20)aryl, (C6-C20)ar(C1-C20)alkyl, (C1-C20)alkyl(C6-C20)aryl, $-NH_2$, $-NHR^a$, $-NR^aR^b$, $-OH$, $-OR^c$, $-SH$, $-SR^d$, $-PH_2$, $-PHR^e$ or $-PR^eR^f$; $R^a$ through $R^f$ independently represent (C1-C20)alkyl, (C3-C8)cycloalkyl, (C6-C20)aryl, (C6-C20)ar(C1-C20)alkyl or (C1-C20)alkyl(C6-C20)aryl; y is an integer from 1 to 30; the alkylene, cycloalkylene, arylene, aralkylene or alkylarylene of W, and the alkyl, cycloalkyl, aryl, aralkyl or alkylaryl of $R^1$ through $R^9$ may be further substituted by one or more substituent(s) selected from a group consisting of $-NR^{11}R^{12}$, $-OR^{13}$, $-CR^{14}R^{15}R^{16}$, $-SR^{17}$ and $-PR^{18}R^{19}$; $R^{11}$ through $R^{19}$ independently represent hydrogen, (C1-C20)alkyl, (C3-C8)cycloalkyl, (C6-C20)aryl, (C6-C20)ar(C1-C20)alkyl or (C1-C20)alkyl(C6-C20)aryl.

11. The process for preparing a scaffold material (SM)-transition metal hydride complex according to claim 10, wherein the organic ligand (L) is selected from those represented by one of the following structural formulas:

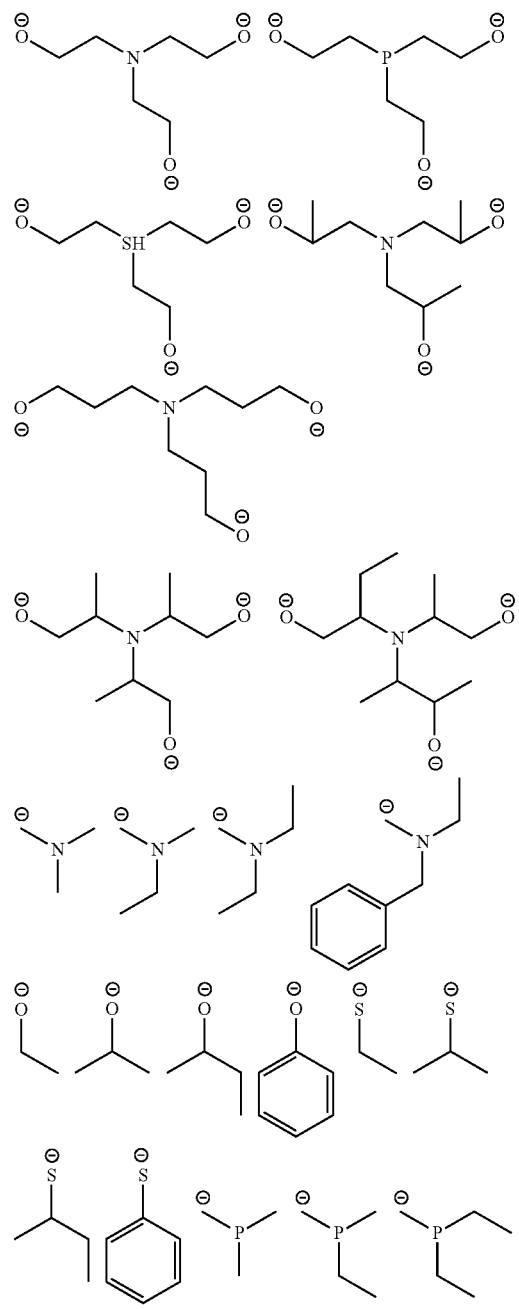

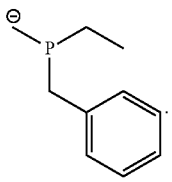

12. The process for preparing a scaffold material (SM)-transition metal hydride complex according to claim 10, wherein the reaction of stage 1) is carried out at reaction temperature of −80~100° C. for reaction duration of 3~50 hours.

13. The process for preparing a scaffold material (SM)-transition metal hydride complex according to claim 10, wherein the reaction mixture after stage 1) and 2) is dried in vacuo for 24 hours with applying Schlenk method, or subjected to chemical extraction process with supercritical $CO_2$.

14. The process for preparing a scaffold material (SM)-transition metal hydride complex according to claim 10, wherein hydrogenation of stage 2) is carried out in gas phase or liquid phase.

15. The process for preparing a scaffold material (SM)-transition metal hydride complex according to claim 14, wherein the gas phase reaction is carried out by using hydrogen, or a mixture of hydrogen and one or more inert gas(es).

16. The process for preparing a scaffold material (SM)-transition metal hydride complex according to claim 14, wherein the liquid phase reaction is carried out by using one or more solvent(s) selected from (C1-C10) saturated aliphatic hydrocarbons and (C6-C20) aromatic hydrocarbons.

17. The process for preparing a scaffold material (SM)-transition metal hydride complex according to claim 15, wherein the gas phase reaction is characterized by reaction temperature of 25~1000° C., reaction pressure of 1~50 atm, and reaction duration of 1~100 hours.

18. The process for preparing a scaffold material (SM)-transition metal hydride complex according to claim 15, wherein the loading of the scaffold material-transition metal ligand complex ([SM]-$M^1L_{(n-1)}$) of Chemical Formula (3) per volume of the reactor in the gas phase reaction is from 0.001 to 1 g/ml.

19. The process for preparing a scaffold material (SM)-transition metal hydride complex according to claim 16, wherein the liquid phase reaction is characterized by reaction temperature of 25~400° C. and reaction duration of 1~100 hours.

20. The process for preparing a scaffold material (SM)-transition metal hydride complex according to claim 16, wherein the scaffold material-transition metal ligand complex ([SM]-$M^1L_{(n-1)}$) of Chemical Formula (3) per volume of the reaction solvent in the liquid phase reaction is from 0.0001 to 1 g/ml.

* * * * *

UNITED STATES PATENT AND TRADEMARK OFFICE
CERTIFICATE OF CORRECTION

PATENT NO.         : 8,536,358 B2                                               Page 1 of 1
APPLICATION NO.    : 13/059345
DATED              : September 17, 2013
INVENTOR(S)        : Jong Sik Kim It is certified that error appears in the above-identified patent and that said Letters Patent is hereby corrected as shown below:

In the Claims

Column 24, Line 14, Claim 3, delete "fullerence" and insert -- fullerene --

Column 24, Line 26, Claim 5, delete "($M^1H_{(n-1:)}$." and insert -- ($M^1H_{(n-1:)}$): --

Column 24, Line 28, Claim 5, delete "$(G^1)_n$-A-$(G^2)_b$," and insert -- $(G^1)_a$-A-$(G^2)_b$ --

Column 24, Line 46, Claim 5, delete "cyclo alkyl," and insert -- cycloalkyl, --

Column 24, Line 53, Claim 6, delete "py-nylene" and insert -- pyrenylene --

Column 25, Line 47, Claim 10, delete "ligand" and insert -- ligand, --

Column 28, Line 25, Claim 20, delete "([SM-$M^1L_{(n-1)}$" and insert -- ([SM-$M^1L_{(n-1)}$) --

Signed and Sealed this
First Day of April, 2014

Michelle K. Lee
*Deputy Director of the United States Patent and Trademark Office*